United States Patent [19]

Siposs et al.

[11] Patent Number: 4,675,010
[45] Date of Patent: Jun. 23, 1987

[54] THORACIC DRAINAGE COLLECTION SYSTEM AND METHOD

[75] Inventors: George G. Siposs, 2855 Valasco La., Costa Mesa, Calif. 92626; Jack J. Sternlieb, Rancho Mirage, Calif.

[73] Assignee: American Omni Medical, Inc., Costa Mesa, Calif. ; by said Jack Sternlieb

[21] Appl. No.: 784,340

[22] Filed: Oct. 4, 1985

[51] Int. Cl.⁴ .............................................. A61M 1/00
[52] U.S. Cl. ..................................... 604/319; 137/205
[58] Field of Search ................................ 604/317–323, 604/49, 405, 406, 408, 411, 415; 137/205; 210/120, 436, 472; 433/91

[56] References Cited

U.S. PATENT DOCUMENTS

| | | | |
|---|---|---|---|
| 3,017,886 | 1/1962 | Thompson | 604/319 |
| 3,545,671 | 12/1970 | Ross | 604/410 |
| 3,556,101 | 1/1971 | Economou | 604/319 |
| 3,768,478 | 10/1973 | Fertik et al. | 640/320 |
| 3,945,392 | 3/1976 | Denton et al. | 137/205 |
| 4,346,711 | 8/1982 | Agdanowski et al. | 604/319 |
| 4,402,687 | 9/1983 | Denty et al. | 604/319 |
| 4,540,413 | 9/1985 | Russo | 604/320 |

Primary Examiner—C. Fred Rosenbaum
Assistant Examiner—J. L. Kruter
Attorney, Agent, or Firm—Allen A. Dicke, Jr.

[57] ABSTRACT

A rigid receptacle has an open top, and a removable lid seals by vacuum onto the open top. The lid carries dependent therefrom into the receptacle a flexible disposable collection bag. The bag is supported from the lid by means of an inlet fitting and an outlet fitting which extends from the lid. The inlet fitting is for attachment to a tube which extends into the thoracic cavity of the patient. The outlet fitting has an outwardly facing check valve therein to prevent buildup of pressure within the collection bag. The lid is also provided with a vacuum connection, by which vacuum can be drawn into the receptacle but outside of the collection bag to close vacuum in the vacuum bag without the need for continuous vacuum or the connection of a vacuum line to the interior of the collection bag.

8 Claims, 5 Drawing Figures

U.S. Patent  Jun. 23, 1987  4,675,010
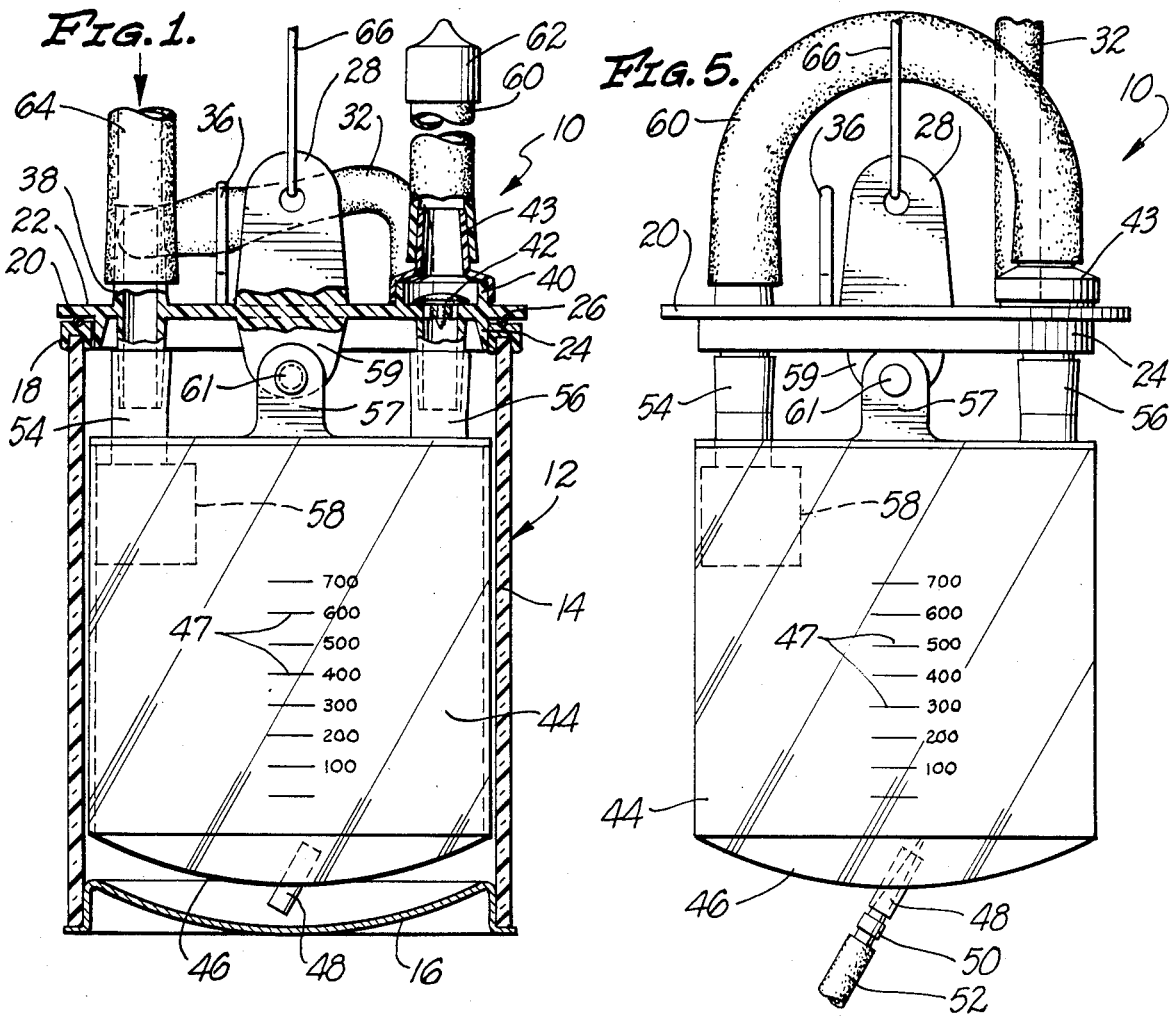
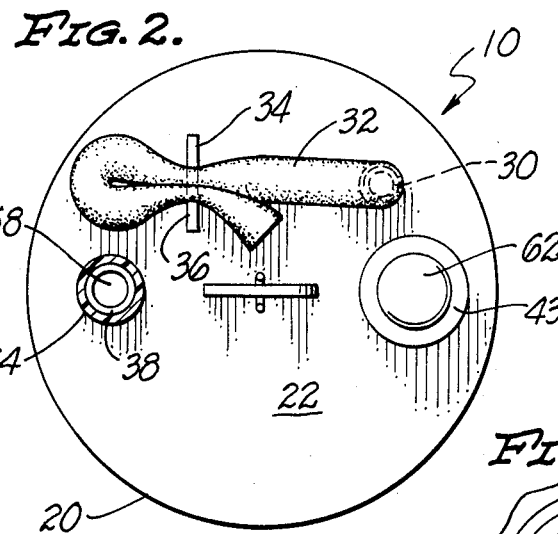
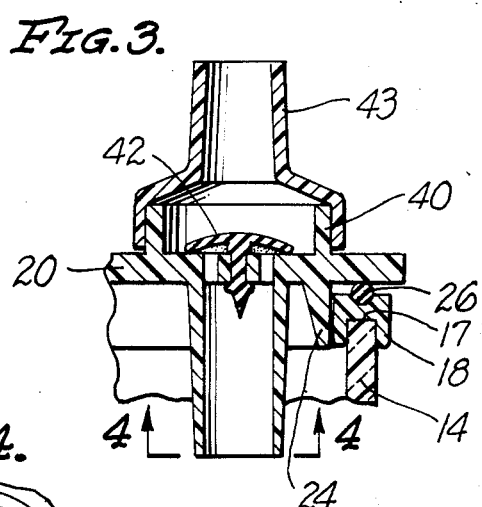
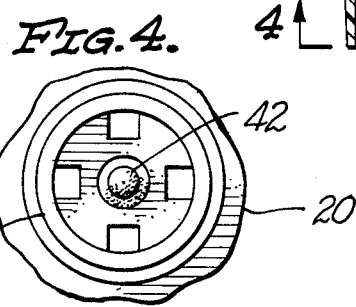

4,675,010

THORACIC DRAINAGE COLLECTION SYSTEM AND METHOD

BACKGROUND OF THE INVENTION

This invention is directed to a thoracic drainage collection system and particularly such a system which conserves the collected fluids in a disposable sterile collection bag and which does not require the continuous application of external suction for causing collection.

After open-heart operations and other operations which require opening of the thoracic cavity, when the chest wound is closed, some fluids still escape into the thoracic cavity of the patient. These fluids must be gently evacuated in an effective manner so as not to collect and cause complications to the patient.

After closing the chest, a tube is usually left with its suction end inside the chest cavity. This tube is connected to a system for evacuation of exudates. Early devices for applying suction and collecting the fluid are shown in U.S. Pat. No. 2,999,500 and U.S. Pat. No. 3,032,037. Later patents have been improvements on these early devices. The later patents are often directed to ways in which the suction from the installed hospital vacuum source is distributed between the collection bag and the receptacle. U.S. Pat. Nos. 3,556,101 and 3,719,197 are such later patents.

A problem which has not been particularly well addressed by the prior art is the situation where air from pneumothorax gets into the suction tubing and the air must be released lest it cause complications to the patient's condition.

There is need for a system which accomplishes thoracic drainage without requiring the use of continuous suction, but is effective and reliable, low in cost, and can be supplied presterilized.

SUMMARY OF THE INVENTION

In order to aid in the understanding of this invention, it can be stated in essentially summary form that it is directed to a thoracic drainage collection system which includes a substantially rigid receptacle having an open top together with a removable lid which seals onto the open top. A flexible disposable collection bag is attached to the open top by means of an inlet fitting connectable to the thorax evacuation tube and an outlet fitting which includes an outwardly directed relief valve (the valve is in the lid, not in the bag) to prevent buildup of pressure within the collection bag. The collection bag is otherwise closed. A vacuum connection permits drawing a vacuum within the receptacle but exteriorly of the collection bag.

It is, thus, an object and advantage of this invention to provide a thoracic drainage collection system which prevents buildup of pressure within a collection bag to prevent pneumothorax.

It is another object and advantage of this invention to provide a flexible disposable collection bag which is connected only to the thorax tube and through an outwardly facing relief valve to atmosphere so that, upon the application of a vacuum to the exterior of the flexible disposable collection bag, the vacuum source can be removed and the collection bag can collect chest cavity fluids. The expanded bag creates vacuum in the patient line and promotes better drainage.

It is a further object and advantage of this invention to provide a pumpless thoracic drainage collection system which can be readily maintained in a sterile condition and which can be economically manufactured and reliably used to provide for sterile thoracic drainage without the continuous use of a vacuum system or suction pump and while maintaining protection against pneumo as well as hemothorax.

Other objects and advantages of this invention will become apparent from a study of the following portion of the specification, the claims and the attached drawings.

BRIEF DESCRIPTION OF THE DRAWINGS

FIG. 1 is a side-elevational view of the thoracic drainage collection system of this invention, with a portion of the top broken away to show the structure on substantially a centerline section.

FIG. 2 is a plan view thereof.

FIG. 3 is an enlarged section through the vent valve.

FIG. 4 is a further enlarged view as seen on the line 4—4 of FIG. 3.

FIG. 5 is a side-elevational view of the filled disposable bag, hung for return of the fluid to the patient.

DESCRIPTION OF THE PREFERRED EMBODIMENT

The thoracic drainage collection system of this invention is generally indicated at 10 in FIGS. 1 and 2. A portion of the system is intended to be used only once, and a portion is intended to be reuseable. The reuseable portion is rigid receptacle 12 which is in the form of a round, open top receptacle with a permanently attached closed bottom cap 16. The walls 14 of the receptacle are preferably in the form of a right circular cylindrical tube. The walls carry permanently attached bottom cap 16 to form the receptacle 12. The walls 14 terminate at the top with a top edge 17. Seal ring 18 is secured on and sealed to the top edge and has an O-ring groove in the top edge in which is positioned O-ring 26 so that the receptacle is suitable for sealing. The receptacle 12 is preferably made of a sterilizable transparent synthetic polymer composition material such as acrylic. Graduations may be marked thereon to indicate the internal volume, but are preferably placed on the bag contained therein.

The disposable portion of the system is the balance of the structure. Lid 20 has a flat top 22 and a downwardly extending lip or flange 24 which fits inside the top portion of walls 14. O-ring seal 26 is engaged between the lid and receptacle to provide a vacuum-tight seal. An O-ring seal is shown engaged between the seal ring 18 and the under side of lid 20. However, seals of other types, such as a flat ring, could be employed when appropriate sealing surfaces are provided. Lid 20 is provided with an eyelet 28 for subsequent support of the lid, as shown in FIG. 3. Nipple 30 is formed on the lid to receive flexible vacuum tube 32. The interior opening in the nipple extends through the lid so that a vacuum drawn on tube 32 is drawn on the interior of the receptacle but outside the bag. Fingers 34 and 36 are formed on the lid, extending upwardly from the top surface thereof, and are sized so that flexible vacuum tube 32 can be folded and pinched therebetween to close off the vacuum tube. This configuration is shown in FIG. 2.

Inlet nipple 38 and vent nipple 40 are also formed on lid 20. The nipples 38 and 40 are each formed with an upstanding portion above the lid onto which a tube can be attached and a downwardly directed portion also on which a tube can be attached. The nipple 40 has an inlet check valve 42 integrally formed therewith. The check valve 42 is preferably a soft flexible mushroom-shaped valve so as to eliminate orientation limitations on operation of the check valve and to permit venting with absolutely minimum valve opening pressure yet provide positive seal in the reverse direction. Fitting 43 reduces the nipple 40 to tubing size.

Collection bag 44 is made of soft, flexible polymer composition material such as polyvinyl chloride. Bag 44 is folded flat in the empty condition and the bottom 46 of the bag is preferably conical. The collection bag 44 and its conical bottom 46 are sized to fit within receptacle 12 so that the bottom of the bag rests on the domed bottom of the receptacle and the walls of the bag substantially fit against the walls of the receptacle, without unduly stretching the bag. The walls of the bag preferably carry volume markings 47 thereon. The bottom of the bag has fitting 48 therein. The fitting 48 is a tube sealed in the bag bottom. The tube has a membrane thereacross. The tube is suitable to accept a conventional blood spike 50 which carries a conventional IV tube 52 for the purpose hereinafter explained.

The upper portion of the collection bag is envelope-sealed around inlet fitting 54 and vent fitting 56. These fittings may be in the form of soft PVC tubing, with the bag flat-sealed therearound to completely seal away the interior of the bag. Filter bag 58 is secured on the lower end of inlet fitting 54 within bag 44. Filter bag 58 is made of polyester of a suitable mesh, such as between 100 and 300 microns, for retaining clots substantially larger than normal blood cells. The fittings 54 and 56 are flexible and, thus, can be attached onto the lower ends of nipples 38 and 40, respectively, as is seen in FIGS. 1 and 5.

A part of the top flat-sealing of the bag is formed into an ear 57 which fits flat against a downwardly projecting flange 59 under the lid to which it is fastened by a snap fastener or button 61 to prevent accidental separation of the bag from the lid.

Vent tube 60 is a flexible tube mounted on fitting 43 on vent nipple 40. Vent tube 60 is sufficiently long to reach inlet nipple 38. Cap 62 is mounted on the free end of vent tube 60 and is a loose cap which permits the vent of air out from under cap 62. Cap 62 is to prevent contamination of the interior of vent tube 60. Patient tube 64 extends into the chest cavity of the patient. The suction end of tube 64 is installed in the operating room and is connected to inlet nipple 38 when suction is desired. Thereupon flexible vacuum tube 32 is connected to the normal hospital vacuum connection. The interior of receptacle 12 is evacuated, but the vacuum is not directly connected to the interior of collection bag 44. Instead, collection bag 44, which was installed in the receptable in flat, collapsed condition, has the below atmospheric pressure of the vacuum transferred through flexure of the walls of the collection bag to the interior space of the collection bag. In this way, the interior of the collection bag exerts suction on patient tube 64.

When the desired level of vacuum is reached within the receptacle outside of the collection bag, flexible vacuum tube is pinched off and is inserted between fingers 34 and 36, as shown in FIG. 2, to maintain the vacuum interiorly of the receptacle. Air cannot enter the receptacle through vacuum nipple 30. In addition, air cannot enter the receptacle or collection bag through vent nipple 40 because of the orientation of vent check valve 42. Thus, the only entrance to the collection bag is through patient tube 64. The suction draws exudates from the chest of the patient into the collection bag. The collection system can be placed close to the patient and need not be connected to a vacuum source. In this way, the patient can be conveniently moved from one location to another without continuous connection to a vacuum source. In addition, the contents of the collection bag are completely separate from other systems, including the vacuum system, to maintain sterility of the collection bag from contamination sources other than the patient, and to prevent contamination of the vacuum system.

In some cases, air pressure builds up in the chest and the air must be released lest it cause pneumothorax. If pressure builds up, the air passes through the patient line into collection bag 44. Since the pressure is above ambient, outlet check valve 42 opens and the air is released through vent tube 60 under cap 62. In this way, pressure buildup is prevented.

After the collection bag is normally filled, it is removed from its receptacle. In order to prevent contamination of the interior of the collection bag, the cap 62 is removed and, when the patient tube 64 is disconnected from inlet nipple 38, the free end of vent tube 60 is placed onto inlet nipple 38, as shown in FIG. 5. Under these circumstances, the interior of the collection bag is closed off to prevent contamination. When it is desired to return the collected fluids to the patient, eyelet 28 is hung on hook 66, which may be on an IV pole. The IV tube 52 connected to blood spike 50 permits intravenous return of the fluids to the patient or drainage to a sealed receptacle. Filter bag 58 retains larger material such as blood clots and, in this way, only benign fluid is returned to the patient.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A thoracic vacuum drainage collection system for collecting shed blood comprising:

a substantially rigid receptacle having an opening;

a lid for positioning over said opening to close said opening, said lid having walls defining an inlet passage and a vent passage through said lid, said walls defining an inlet passage comprising an inlet nipple through said lid extending both within and without said lid and said walls defining said vent passage comprising a nipple extending both within and without said lid, a flexible tube mounted on said vent nipple on the exterior of said lid and said flexible tube being sufficiently long to engage over said inlet nipple exterior of said lid to close the interior of said collection bag to prevent contaminants from entering said collection bag and to prevent bag contents from being outwardly spilled;

a flexible collection bag, said flexible collection bag having an inlet fitting fastened to said walls defining said inlet passage and a vent secured to said walls defining said vent passage, means associated with said vent passage for preventing fluid entry into said flexible bag through said vent passage;

a blood spike membrane in said collection bag so that fluid therein can be drained out through a blood spike;

fastening means on said lid for supporting said lid and said collection bag independently of said receptacle to drain fluid out of said collection bag through a blood spike;

a separate suction passage on said lid for drawing a vacuum within said receptacle, said suction passage being connected only exteriorly of said collection bag and being unconnected to the interior of said collection bag, said separate suction passage having disconnection means associated therewith for disconnecting the interior of said receptacle from the vacuum source after the vacuum is drawn to expand said collection bag into said receptacle so that inlet into said collection bag is only through said inlet passage.

2. A thoracic vacuum drainage collection system for collecting shed blood comprising:

a substantially rigid receptacle having an opening;

a lid for positioning over said opening to close said opening, said lid having walls defining an inlet passage and a vent passage through said lid, said walls defining an inlet passage comprise an inlet nipple through said lid extending both within and without said lid and said walls defining said vent passage comprise a nipple through said lid extending both within and without said lid, a flexible tube mounted on said vent nipple on the exterior of said lid, said flexible tube being sufficiently long to engage over said inlet nipple exterior of said lid to close the interior of said collection bag to prevent contaminants from entering said collection bag a flexible collection bag, said flexible collection bag having an inlet fitting fastened to said walls defining said inlet passage and a vent secured to said walls defining said vent passage, means associated with said vent passage for preventing fluid entry into said flexible bag through said vent passage;

a blood spike membrane in said collection bag so that fluid therein can be drained out through a blood spike;

fastening means on said lid for supporting said lid and said collection bag independently of said receptacle to drain fluid out of said collection bag through a blood spike;

a separate suction passage on said lid for drawing a vacuum within said receptacle, said suction passage being connected only exteriorly of said collection bag and being unconnected to the interior of said collection bag, said separate suction passage having disconnection means associated therewith for disconnecting the interior of said receptacle from the vacuum source after the vacuum is drawn to expand said collection bag into said receptacle so that inlet into said collection bag is only through said inlet pasage.

3. The system of claim 2 wherein said means for preventing inflow through said vent is an outwardly directed check valve.

4. A thoracic vacuum drainage collection system for collecting shed blood comprising:

a substantially rigid receptacle having an opening;

a lid for positioning over said opening to close said opening, first and second spaced fingers on the exterior of said lid, said lid having walls defining an inlet passage and a vent passage through said lid;

a flexible collection bag, said flexible collection bag having an inlet fitting fastened to said walls defining said inlet passage and a vent secured to said walls defining said vent passage, means associated with said vent passage for preventing fluid entry into said flexible bag through said vent passage;

a separate suction passage on said lid for drawing a vacuum within said receptacle, said suction passage being connected only exteriorly of said collection bag and being unconnected to the interior of said collection bag, said passage including a suction nipple on said lid having said suction passage through said lid, and a flexible vacuum tube mounted on said vacuum nipple, said flexible vacuum tube being closeable to prevent air passage therethrough, said fingers being spaced so that when said vacuum tube is thrust therebetween, said vacuum tube is pinched off to prevent air flow therethrough so that the inlet into said collection bag is only through said inlet passage.

5. The system of claim 4 wherein said walls defining an inlet passage comprise an inlet nipple through said top extending both within and without said top and said walls defining said vent passage comprise a nipple extending both within and without said lid.

6. The method of collecting thoracic drainage comprising the steps of:

placing a sterile flexible collection bag within a rigid receptacle and closing the receptacle;

placing a sterile flexible collection bag within a rigid receptacle and closing the receptacle;

opening the interior of the flexible collection bag to the atmosphere;

connecting the flexible collection bag with the atmosphere through an outwardly facing check valve to permit fluid flow from the collection bag to the atmosphere through the check valve and inhibit flow from the atmosphere into the collection bag through the check valve;

drawing a vacuum on the exterior of the collection bag by withdrawing air only from the space interiorly of the receptacle and exteriorly of the collection bag;

disconnecting the receptacle from the vacuum source when the flexible collection bag is fully expanded into the receptacle;

draining the thoracic fluid through a drain line into the flexible collection bag through a patient tube; and removing the patient tube and connecting a vent tube from a vent connection to the inlet connection.

7. The method of claim 6 further including the step of removing the collection bag from the receptacle;

penetrating the collection bag with a blood spike; and draining the collection bag back to the patient.

8. The method of collecting thoracic drainage comprising the steps of:

placing a sterile flexible collection bag within a rigid receptacle and closing the receptacle;

opening the interior of the flexible collection bag to the atmosphere;

connecting the flexible collection bag with the atmosphere through an outwardly facing check valve to permit fluid flow from the collection bag to the atmosphere through the check valve and inhibit flow from the atmosphere into the collection bag through the check valve;

drawing a vacuum on the exterior of the collection bag by withdrawing air only from the space interiorly of the receptacle and exteriorly of the collection bag;

disconnecting the receptacle from the vacuum source when the flexible collection bag is fully expanded into the receptacle;

draining the thoracic fluid through a drain line into the flexible collection bag through a patient tube;

removing the collection bag from the receptacle;

penetrating the collection bag with a blood spike; and draining the collection bag back to the patient.

* * * * *